(12) United States Patent
    Wohl (10) Patent No.: US 11,033,258 B2
(45) Date of Patent: Jun. 15, 2021

(54) TONGUE ELEVATOR DEVICE

(71) Applicant: Daniel L. Wohl, Jacksonville, FL (US)

(72) Inventor: Daniel L. Wohl, Jacksonville, FL (US)

( * ) Notice: Subject to any disclaimer, the term of this patent is extended or adjusted under 35 U.S.C. 154(b) by 119 days.

(21) Appl. No.: 16/583,842

(22) Filed: Sep. 26, 2019

(65) Prior Publication Data
US 2020/0093471 A1    Mar. 26, 2020

Related U.S. Application Data

(60) Provisional application No. 62/736,594, filed on Sep. 26, 2018.

(51) Int. Cl.
| | |
|---|---|
| A61B 5/00 | (2006.01) |
| A61B 17/24 | (2006.01) |
| A61B 1/24 | (2006.01) |
| A61B 17/02 | (2006.01) |
| A61B 90/00 | (2016.01) |
| A61B 17/00 | (2006.01) |

(52) U.S. Cl.
CPC ................ *A61B 17/02* (2013.01); *A61B 1/24* (2013.01); *A61B 5/4552* (2013.01); *A61B 17/24* (2013.01); *A61B 2017/00814* (2013.01); *A61B 2090/061* (2016.02)

(58) Field of Classification Search
CPC ......... A61B 1/24; A61B 5/4552; A61B 13/00; A61B 2017/00814; A61B 17/02; A61B 17/24
See application file for complete search history.

(56) References Cited

U.S. PATENT DOCUMENTS

| | | | |
|---|---|---|---|
| 2,437,812 A | 10/1944 | Freel | |
| 3,890,960 A * | 6/1975 | Wunsch | A61B 1/24 600/191 |
| 4,655,223 A | 4/1987 | Kim | |
| 4,718,662 A | 1/1988 | North | |
| 5,718,243 A | 2/1998 | Weatherford et al. | |
| D724,729 S * | 3/2015 | Bennett | D24/136 |
| 10,064,614 B2 * | 9/2018 | Tran | B29C 64/386 |
| 2005/0065411 A1 * | 3/2005 | Baldwin | A61B 1/32 600/240 |
| 2015/0265267 A1 | 9/2015 | Tran et al. | |
| 2016/0302809 A1 | 10/2016 | Botzer et al. | |

FOREIGN PATENT DOCUMENTS

| | | |
|---|---|---|
| CN | 202776396 U | 9/2012 |
| CN | 103654704 A | 12/2013 |
| WO | 2015083146 A1 | 6/2015 |

* cited by examiner

*Primary Examiner* — Larry E Waggle, Jr.
(74) *Attorney, Agent, or Firm* — Thomas C. Saitta (57) ABSTRACT

A tongue elevator device is a unitary body having a handle portion, an elongated neck portion and a manipulator end portion. The handle preferably has an oblong main body having a relatively thin flat portion and a relatively thick transversely-extending end portion for secure and comfortable gripping between the fingers and thumb of the user. The elongated neck portion extends distally from the flat portion of the handle portion, and is preferably provided with measuring indicia to visually illustrate distances from the manipulator end portion of the device. The manipulator end portion has a concave distal edge, which may be formed angularly or arcuately, and a central recess or slot is provided in the concave distal edge to receive the frenulum tissue.

16 Claims, 12 Drawing Sheets

TONGUE ELEVATOR DEVICE

BACKGROUND OF THE INVENTION

This application relates generally to the field of devices used in the treatment of ankyloglossia, and more particularly relates to devices utilized to spread or manipulate tissue to prevent reattachment of separated tissue after performance of a lingual frenulotomy, also referred to as a frenotomy or frenectomy.

The lingual frenulum is a small fold of mucous membrane tissue of variable thickness extending from the floor of the mouth to the midline of the underside of the tongue. The frenulum restricts movement of the tip of tongue, limiting thrust as well as restricting overall tongue lift. Formed during embryonic development, over time the frenulum normally retracts from the tip of the tongue to allow increased tongue mobility.

Ankyloglossia is a congenital oral anomaly occurring in infants wherein the lingual frenulum does not fully retract and instead remains connected to the forward portion of the tongue, and in severe cases remains connected to the tip of the tongue so as to fully tether the tongue to the floor of the mouth, with variable presentation or degrees of movement restriction. Because of this, it is common to refer to a person suffering the condition as being tongue-tied. If not corrected, ankyloglossia may result in difficulty in nursing, speech impediments, and poor oral hygiene.

To correct the condition, a frenulotomy is surgically performed wherein the frenulum is severed to release the tongue. It is necessary after the frenulotomy to prevent reattachment of the severed tissue to the tongue during the healing process, which may take up to six weeks. To this end, caregivers and parents are commonly instructed to periodically insert their fingers, a tongue depressor, a cotton swab or the like into the mouth of the infant to spread and separate the severed tissues, to elevate and extend the tongue, and to assist the infant in exercising the tongue until full healing is achieved. Because of the delicate nature of the tissue, caregivers and parents are typically hesitant or distressed in performance of this task, being unsure as to how much pressure to apply, how much extension of the tongue is optimal, and are concerned about damage or infection from fingernails.

To address these problems, tongue elevator or spreader devices have been provided. For example, U.S. Published Patent Application No. 2016/0302809 to Botzer et al. discloses a frenulum spreader that mounts onto the tip of a finger, the device having a pair of flat tips with extending tines that are mounted onto a sheath member. International Application No. WO 2015/083146 to Botzer et al. discloses a tongue elevator having a pair of opposing elongated members hinged to allow the members to be spread apart, each member having a groove or notch disposed the distal end.

It is an object of this invention to provide a tongue elevator or spreader device of improved design, structure and function, the device having an optimal shape for contact with the tissue, measuring indicia to provide a visual indication of the extension amount, and an ergonomically-designed handle for easing gripping and manipulation of the device. The device is manufactured of a material that is easily cleaned and sterilized, and offers an alternative to finger insertion and manipulation that is readily accepted by caregivers and parents.

SUMMARY OF THE INVENTION

The invention in various embodiments comprises in general a device for preventing tongue or lingual frenulum reformation or reattachment after the performance of a frenulotomy, the device being a handheld tongue elevator or spreader device shaped such that the distal end of the device is easily inserted into the oral cavity beneath the tongue to apply pressure against the severed tissue and to provide a means to elevate the tongue itself.

In a first embodiment, the device comprises a handle or gripping portion, an elongated neck portion, and a tissue manipulator end portion. The handle portion is sized and configuration to be easily, comfortably and securely gripped between the thumb and forefinger of the user. In a preferred embodiment the handle portion comprises an oblong or elliptically shaped body having a relatively thin, flat distal portion and a relatively thick, transversely-extending, proximal portion. The elongated neck portion extends in the distal direction from the flat portion of the handle portion, and the manipulator end portion is joined to the neck portion at a transition zone. The transition zone preferably comprises an angled junction. The neck portion and the manipulator end portion are preferably provided with visible measuring indicia to indicate distances from the manipulator end portion of the device. The manipulator end portion, in this embodiment being the distal end of the device with the handle portion being the proximal end of the device, is preferably wider than the neck portion and comprises a concave distal edge, a laterally extending manipulating member and a recess, slot or groove centrally disposed in the concave distal edge. The concave edge may be formed angularly or arcuately and the configuration, width and length of the central recess may vary, such that in some embodiments the combination of the elongated neck portion and the manipulator end portion present an overall configuration similar to the shape of a fish or whale tail.

In an alternative embodiment, the tongue elevator device comprises a centrally located handle having opposing neck portions extending therefrom, with a manipulator end portion connected to each neck portion. In this embodiment the central handle is preferably symmetrically configured so as to present an optimal gripping surface and structure regardless of which manipulator end portion is inserted into the oral cavity. This design allows for a single tongue elevator device wherein the size and/or configuration of the two manipulator end portions are different.

The invention can be further summarized as a tongue elevator device comprising a handle portion, a neck portion and a manipulating end portion, said neck portion connecting said handle portion to said manipulating end portion; said handle portion being wider than said neck portion and said manipulating portion; and said manipulating end portion comprising a distal concave edge and a frenulum recess centrally disposed on said distal concave edge. Furthermore, such device wherein said neck portion and said manipulating end portion are not co-planar and said manipulating end portion extends downwardly from said neck portion; further comprising measuring indicia located on said neck portion; wherein said handle portion comprises a flat portion and a transversely extending, proximal end portion, said proximal end portion being thicker than said flat portion; wherein said proximal end portion is arcuate; wherein said distal concave edge is angular with linear segments; wherein said distal concave edge is arcuate with curved segments; wherein said manipulating end portion is joined to said neck portion at a transition zone; wherein said transition zone is angular; wherein said transition zone comprises an angle between 15 and 25 degrees; wherein said transition zone comprises an angle of approximately 20 degrees; wherein said handle portion is oblong and widest in the transverse direction;

further comprising measuring indicia located on said neck portion and on said manipulating end portion; wherein said neck portion is a first neck portion and said manipulating end portion is a first manipulating end portion, and wherein said device further comprises a second neck portion and a second manipulating end portion; wherein said second neck portion is joined to said handle portion opposite from said first neck portion; and/or wherein said second neck portion and said second manipulating end portion are not co-planar and said second manipulating end portion extends from said neck portion in opposite direction from said first manipulating end portion.

Alternatively, the invention is a tongue elevator device comprising a handle portion, a neck portion and a manipulating end portion, said neck portion connecting said handle portion to said manipulating end portion; said handle portion being wider than said neck portion and said manipulating portion; said manipulating end portion comprising a distal concave edge and a frenulum recess centrally disposed on said distal concave edge; wherein said neck portion and said manipulating end portion are not co-planar and said manipulating end portion extends downwardly from said neck portion, and wherein said manipulating end portion is joined to said neck portion at a transition zone; wherein said handle portion comprises a flat portion and a transversely extending, arcuate, proximal end portion, said proximal end portion being thicker than said flat portion; and further comprising measuring indicia located on said neck portion and said manipulating end portion. Furthermore, such invention wherein said distal concave edge is angular with linear segments; wherein said distal concave edge is arcuate with curved segments; wherein said transition zone is angular; and/or wherein said neck portion is a first neck portion and said manipulating end portion is a first manipulating end portion, and wherein said device further comprises a second neck portion and a second manipulating end portion; wherein said second neck portion is joined to said handle portion opposite from said first neck portion; and wherein said second neck portion and said second manipulating end portion are not co-planar and said second manipulating end portion extends from said neck portion in opposite direction from said first manipulating end portion.

DETAILED DESCRIPTION OF THE INVENTION

As used herein, the terms distal and proximal are used relative to the orientation of the device when the device is inserted into the oral cavity for manipulation of the tissue and tongue, such that the distal direction is the direction toward the back of oral cavity and the proximal direction is the direction toward to the front of the oral cavity. The terms transverse and lateral are used herein as being the direction generally perpendicular to a longitudinal axis defined by the distal and proximal directions. The terms upper and lower are used relative to the orientation of the device when the device is inserted into the oral cavity for manipulation of the tissue and tongue, such that the upper direction is the direction toward the top of oral cavity and the lower direction is the direction toward to the bottom of the oral cavity.

In general, the invention in various embodiments comprises a handheld tongue spreader or elevator device 10. In a first embodiment, as shown in FIGS. 1-8, the tongue elevator device 10 is a unitary member comprising a handle or gripping portion 20, an elongated neck portion 30 and a manipulator end portion 40. The handle portion 20 preferably comprises a main body 21, preferably oblong or elliptical in configuration with a transversely extending long axis, such that the handle portion is widest in the transverse direction. Preferably, the handle portion 20 is wider in the transverse direction then the neck portion 30 or the manipulator end portion 40, and is preferably at least twice as wide. The main body 21 comprises two regions, a distal flat portion 23 and a transversely-extending, preferably arcuate, proximal end portion 24, the thickness of the proximal end portion 24 being greater that the thickness of the distal flat portion 23 so as to present a ridge or shoulder configuration. With this structure the combination of the relatively thin distal flat portion 23 and the relatively thick proximal end portion 24 provide a configuration for the handle portion 20 optimized for secure and comfortable gripping between the finger and thumb of the user.

The elongated neck portion 30 extends distally from distal flat portion 23 of the handle portion 20. The neck portion 30 presents an upper side 32 and a lower side 33. Preferably at least the neck portion 30 and most preferably the neck portion 30 and manipulator end portion 40 are provided with measuring indicia 31 on the upper side 32, such as raised, inscribed or printed elements, the measuring indicia 31 visually illustrating distances along the neck portion 30 from the manipulator end 40 of the device 10. The neck portion 30 is preferably of significantly smaller dimension in the transverse direction than the handle portion 20, i.e., the handle portion 20 is wider than the neck portion 30.

Figure 1:
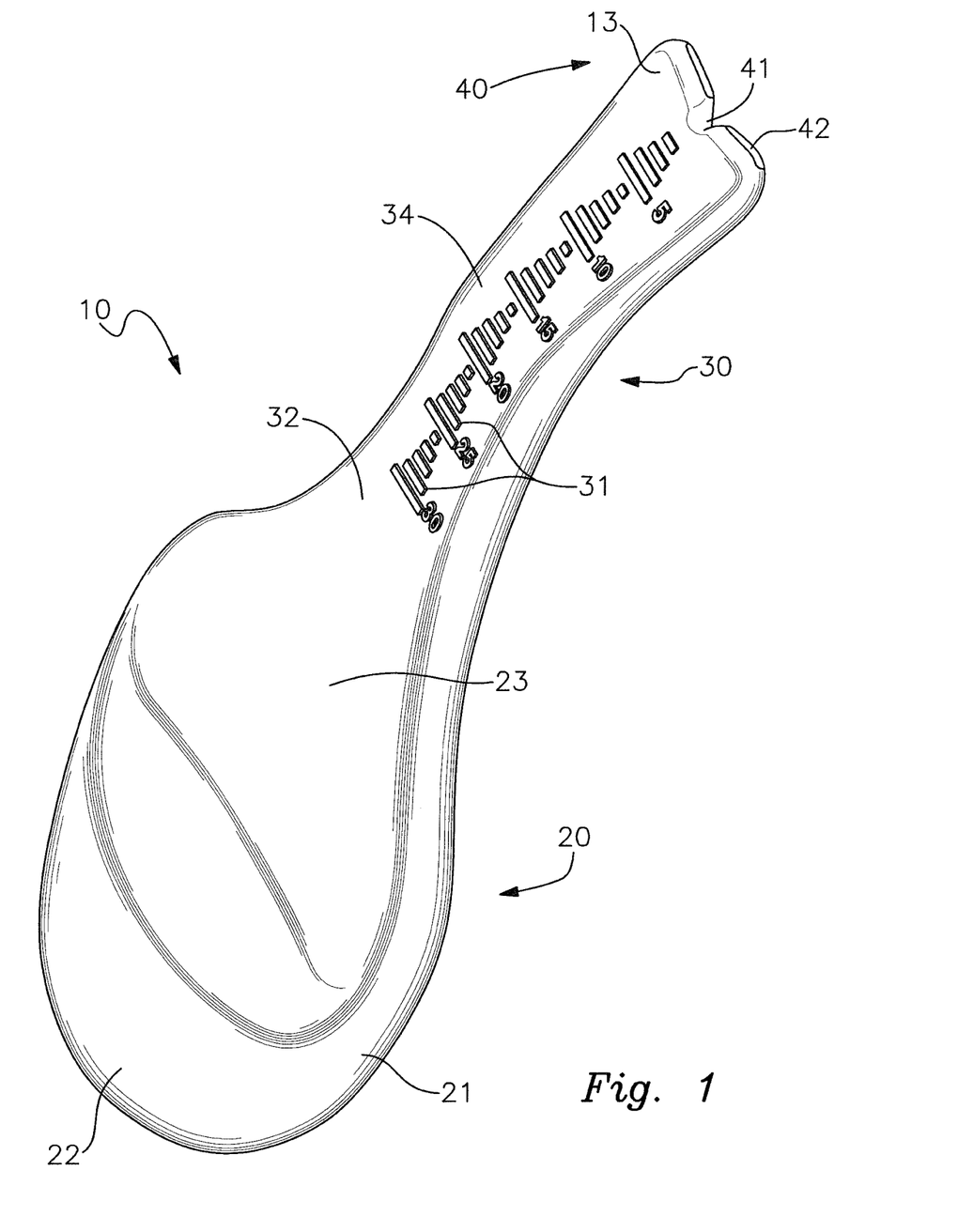
FIG. 1 is perspective view of a first embodiment of the tongue elevator device, wherein the concave edge of the manipulator end portion of the tongue elevator device is shown as being substantially angular.
Figure 2:
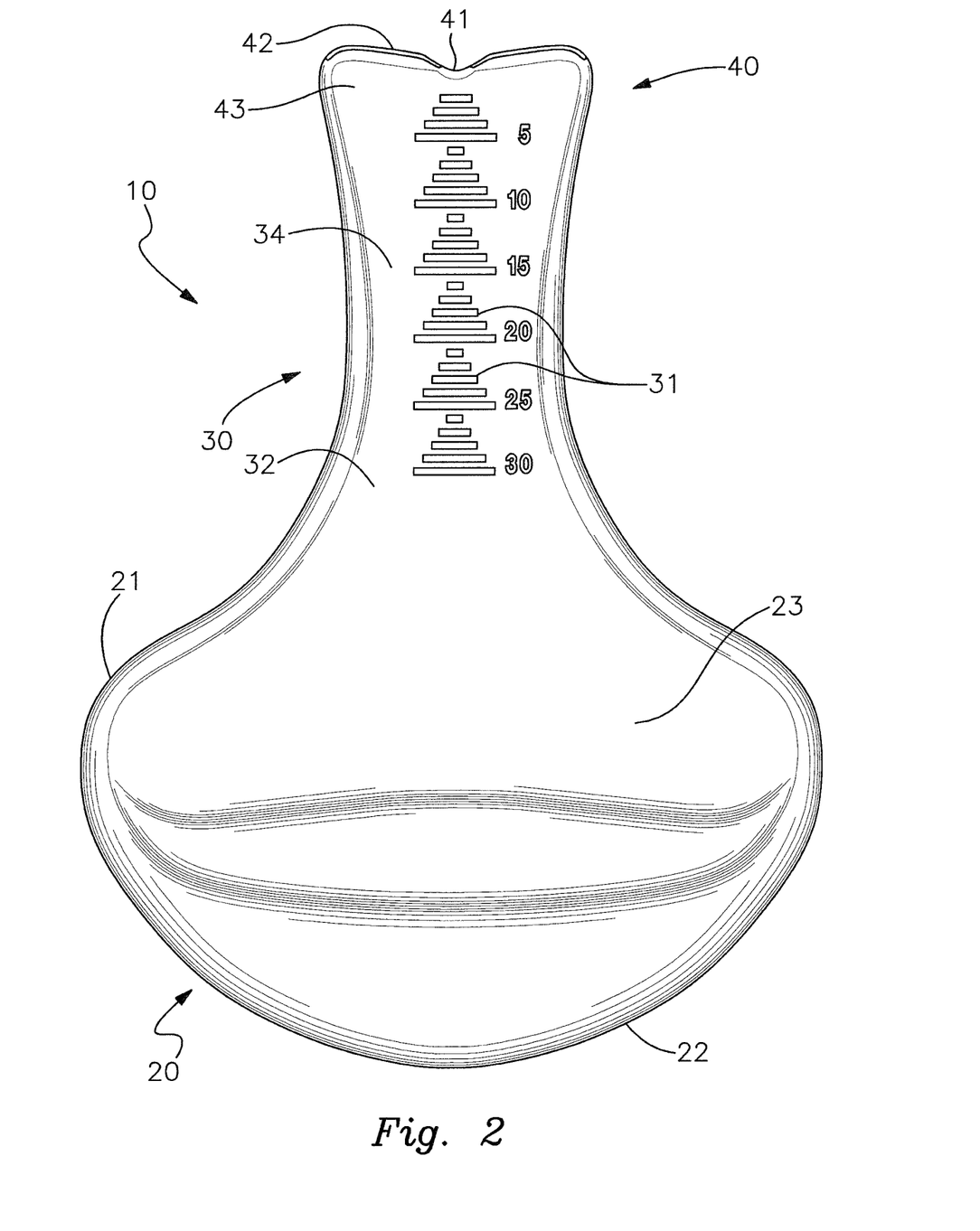
FIG. 2 is a top view of the embodiment of FIG. 1 showing the upper side of the neck portion.
Figure 3:
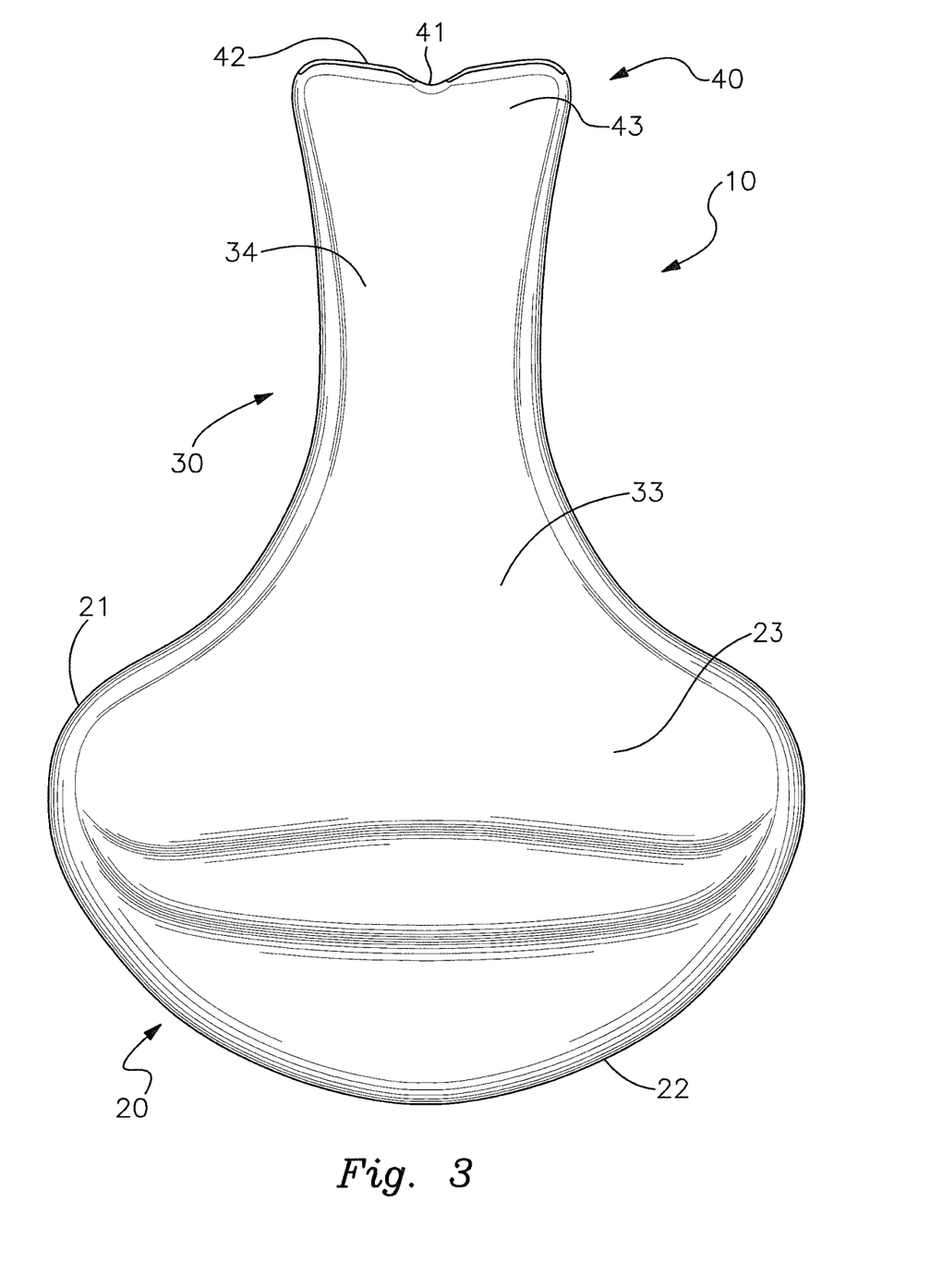
FIG. 3 is a bottom view of the embodiment of FIG. 1 showing the lower side of the neck portion.
Figure 4:
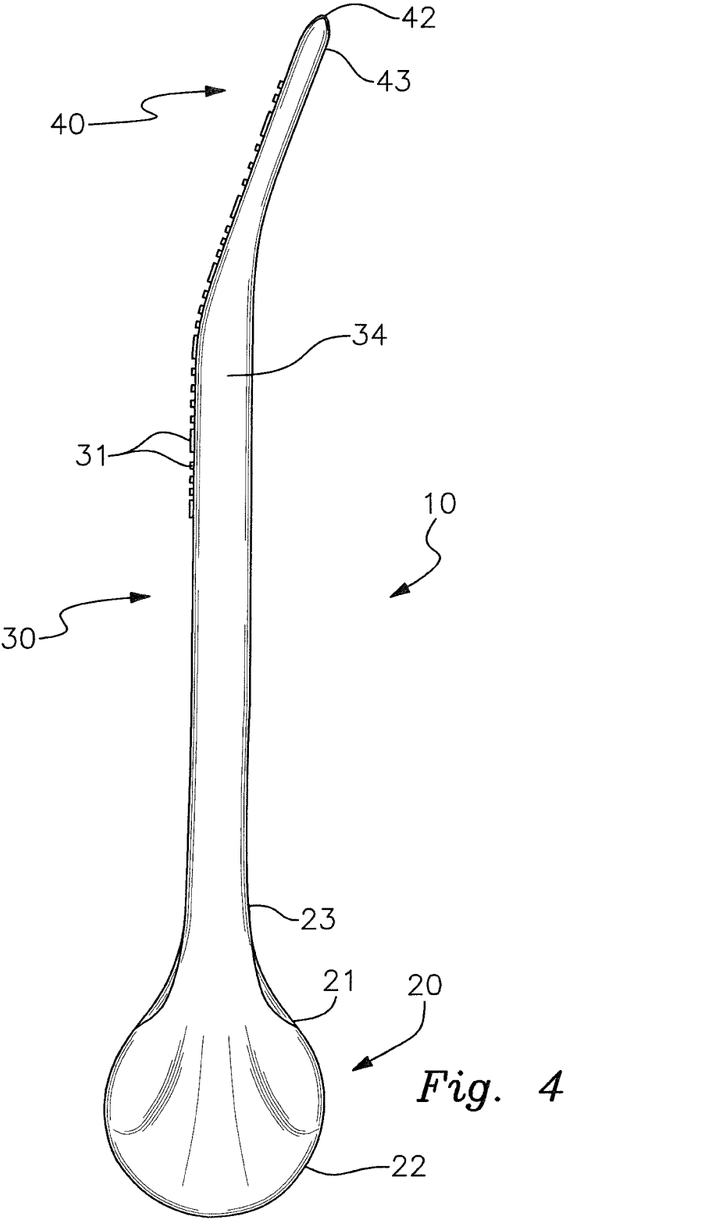
FIG. 4 is a lateral or side view of the embodiment of FIG. 1.
Figure 5:
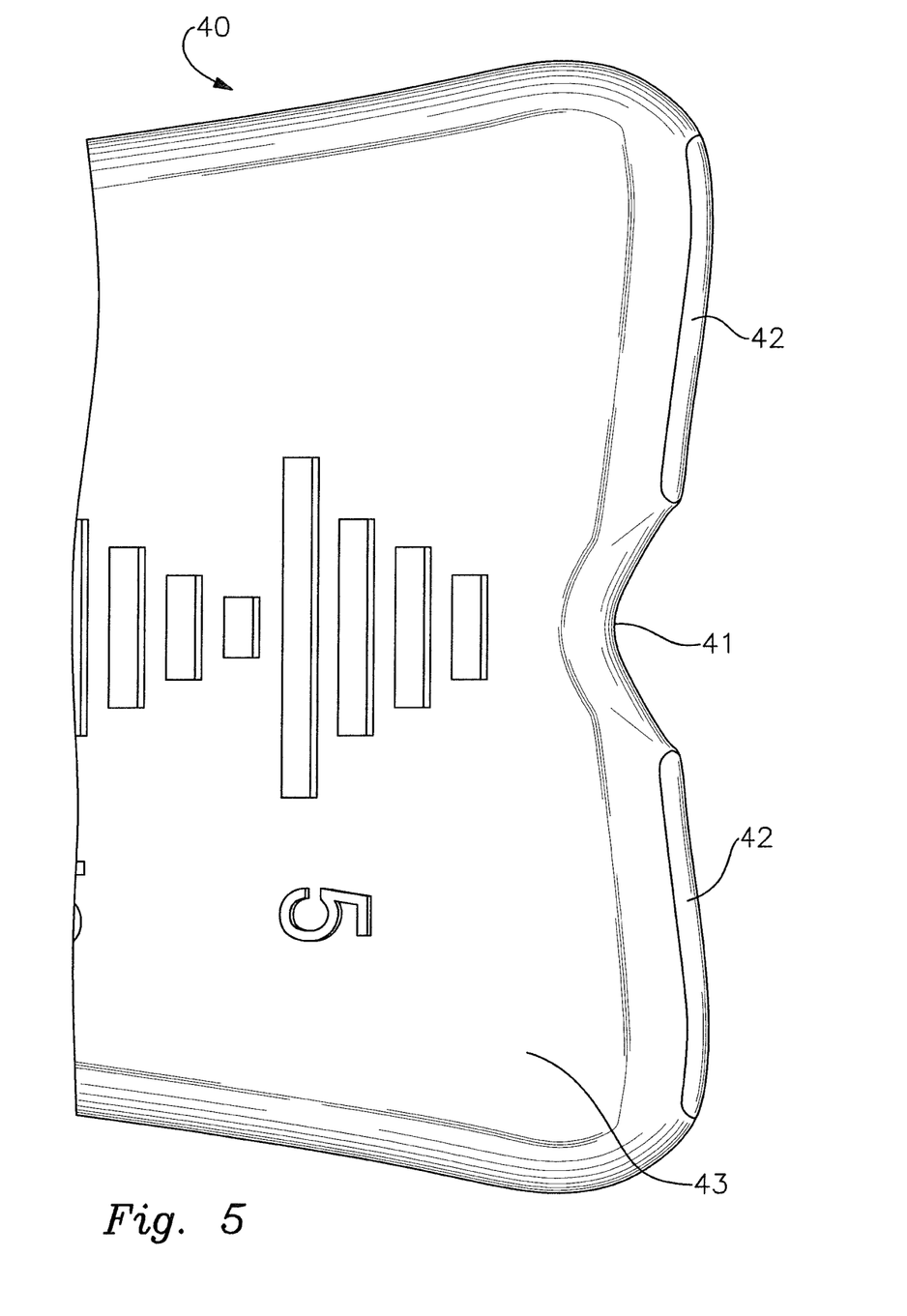
FIG. 5 is a partial top view of the embodiment of FIG. 1 showing the manipulator end portion.
Figure 6:
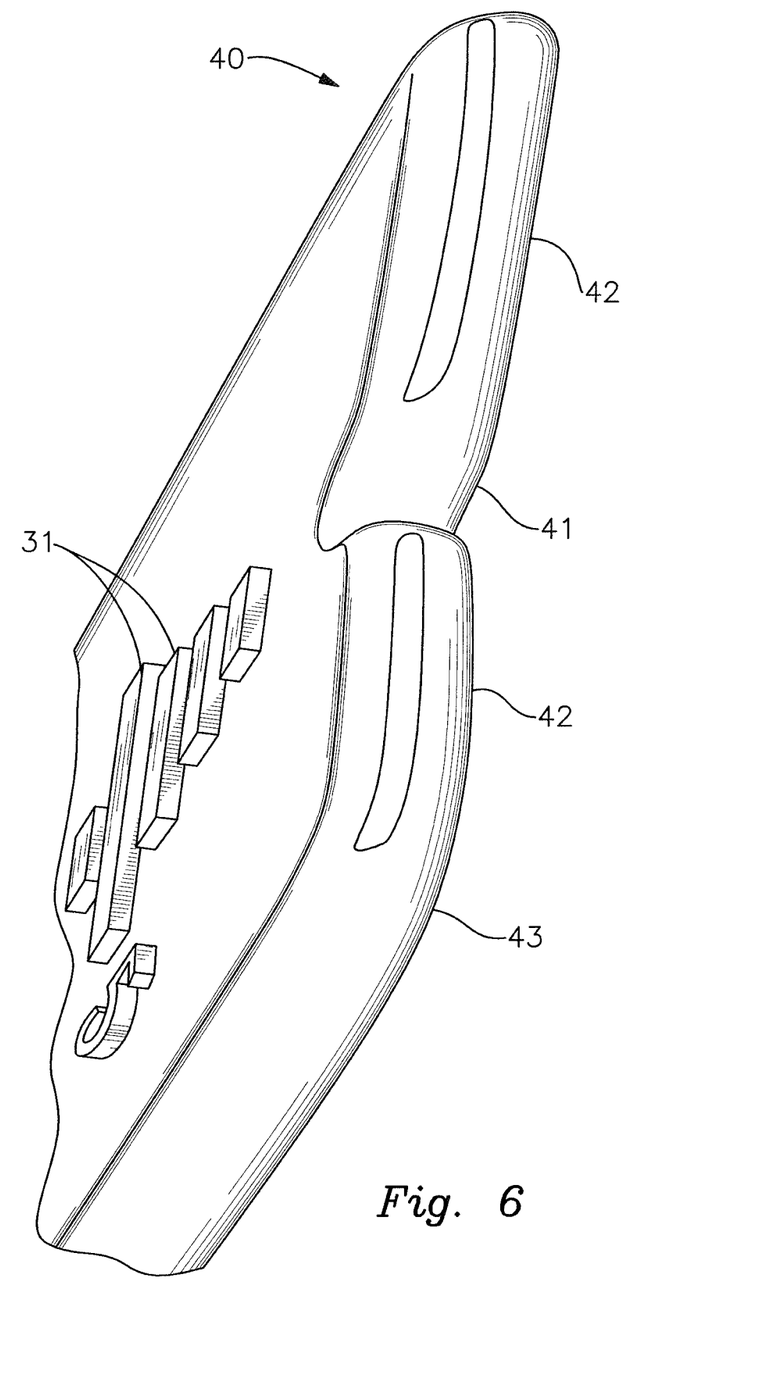
FIG. 6 is a partial perspective view of the embodiment of FIG. 1 showing the manipulator end portion.
Figure 7:
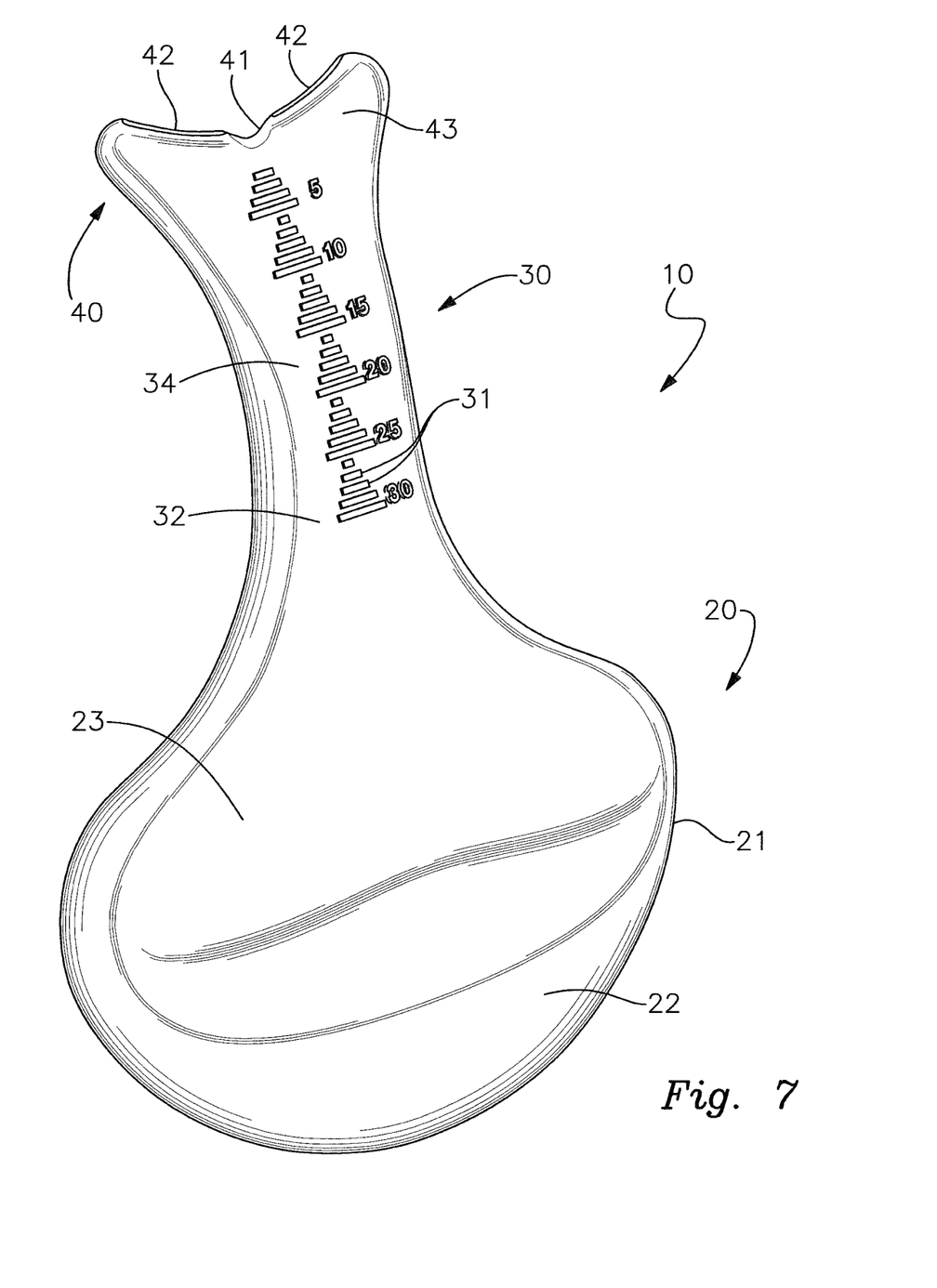
FIG. 7 is a perspective view of an alternative embodiment of the tongue elevator device wherein the concave edge of the manipulator end portion is shown as being substantially arcuate.
Figure 8:
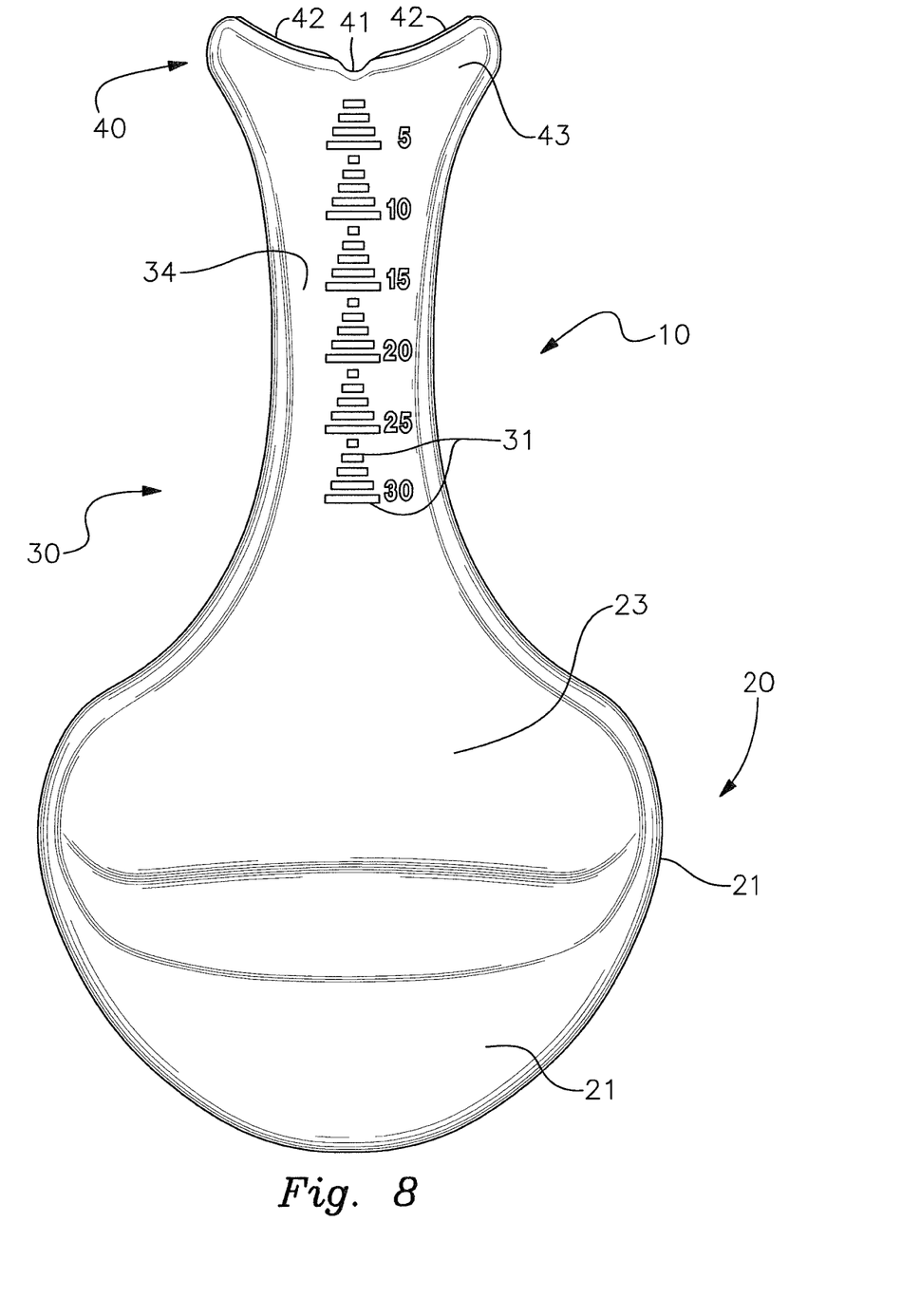
FIG. 8 is a top view of the embodiment of FIG. 7.
Figure 9:
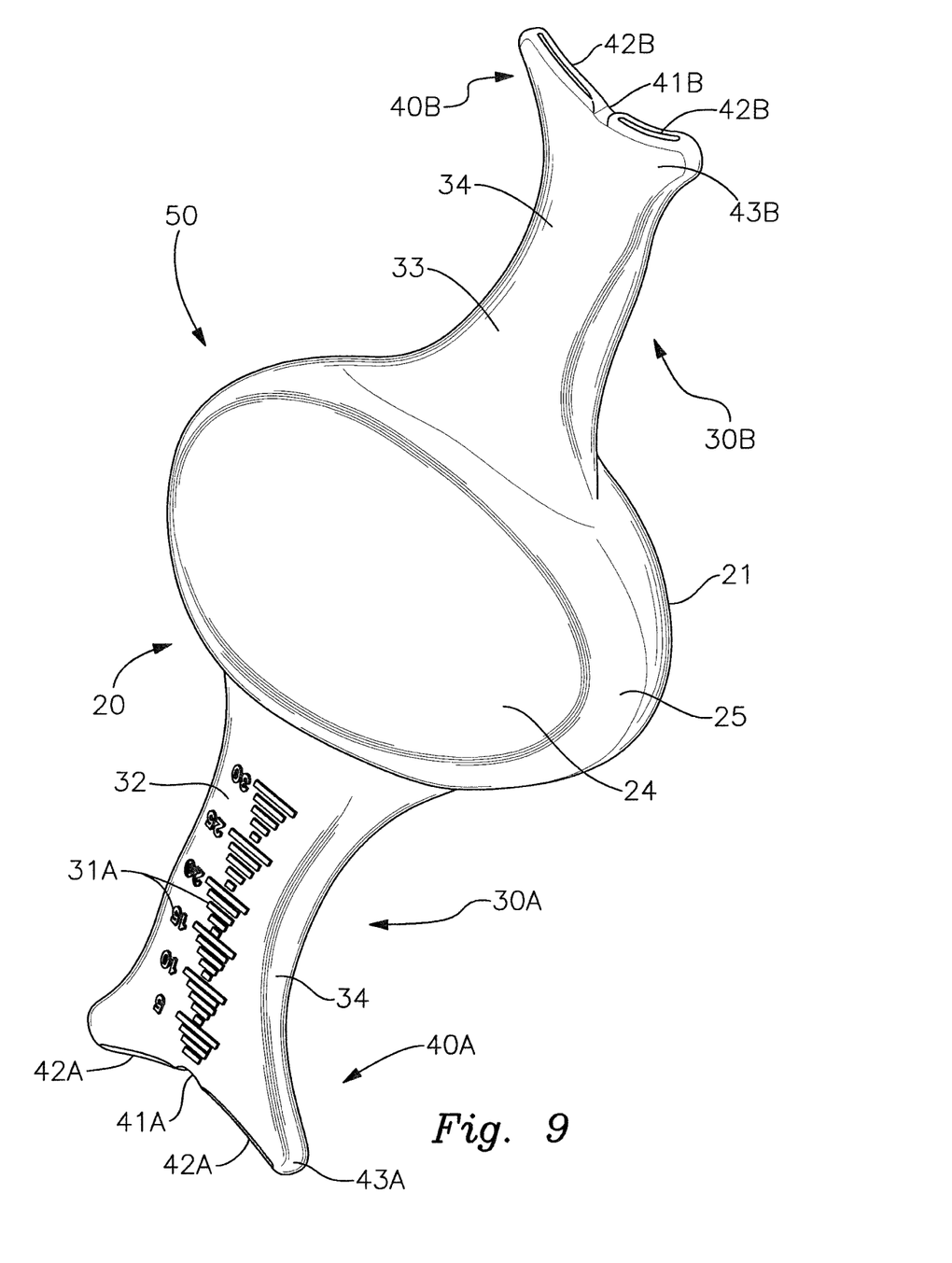
FIG. 9 is a perspective view of a first side of an alternative embodiment of the tongue elevator showing a pair of opposing neck portions and manipulator end portions, the manipulator end portions being of different configurations.
Figure 10:
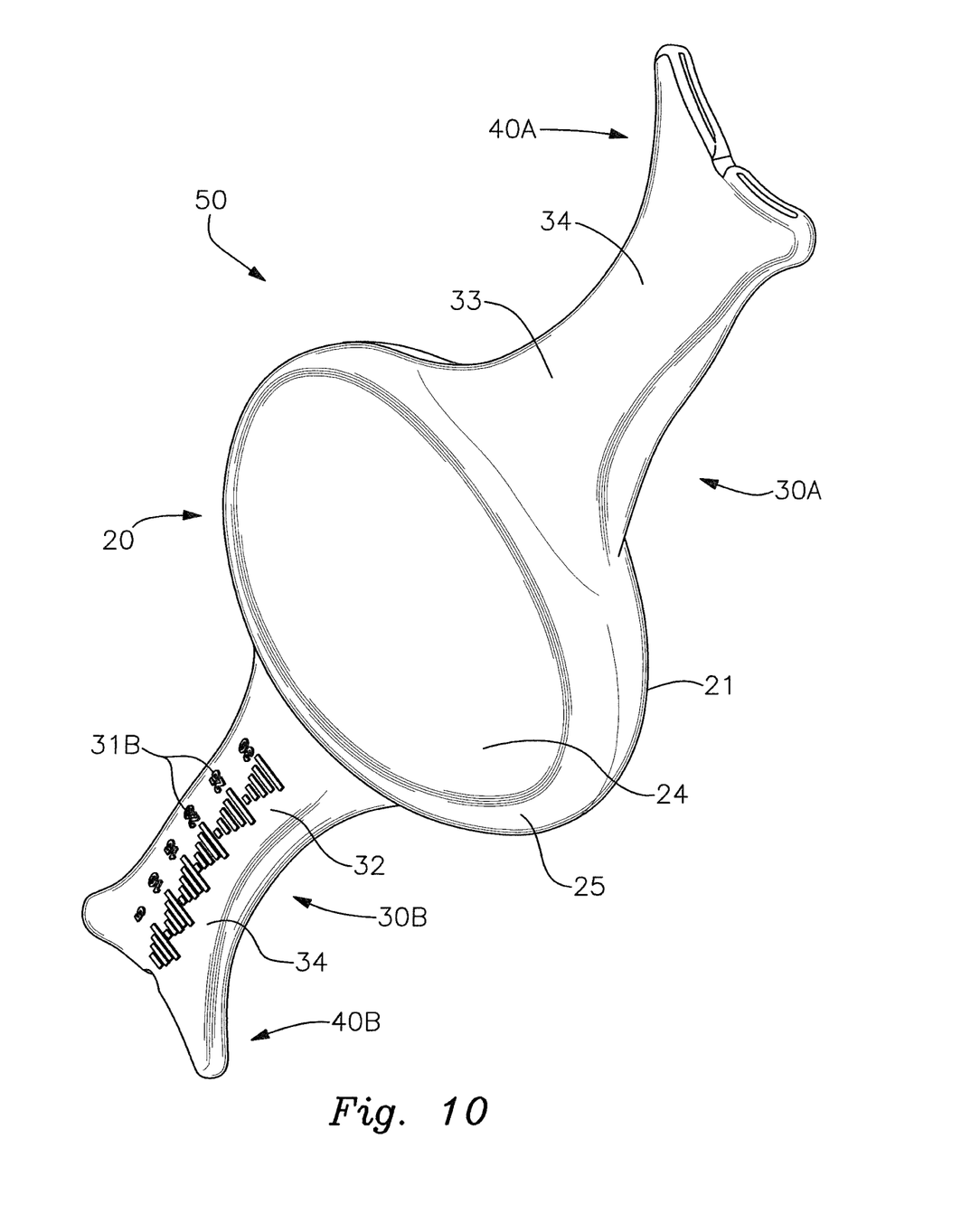
FIG. 10 is a perspective view of the opposite side of the embodiment of FIG. 9.
Figure 11:
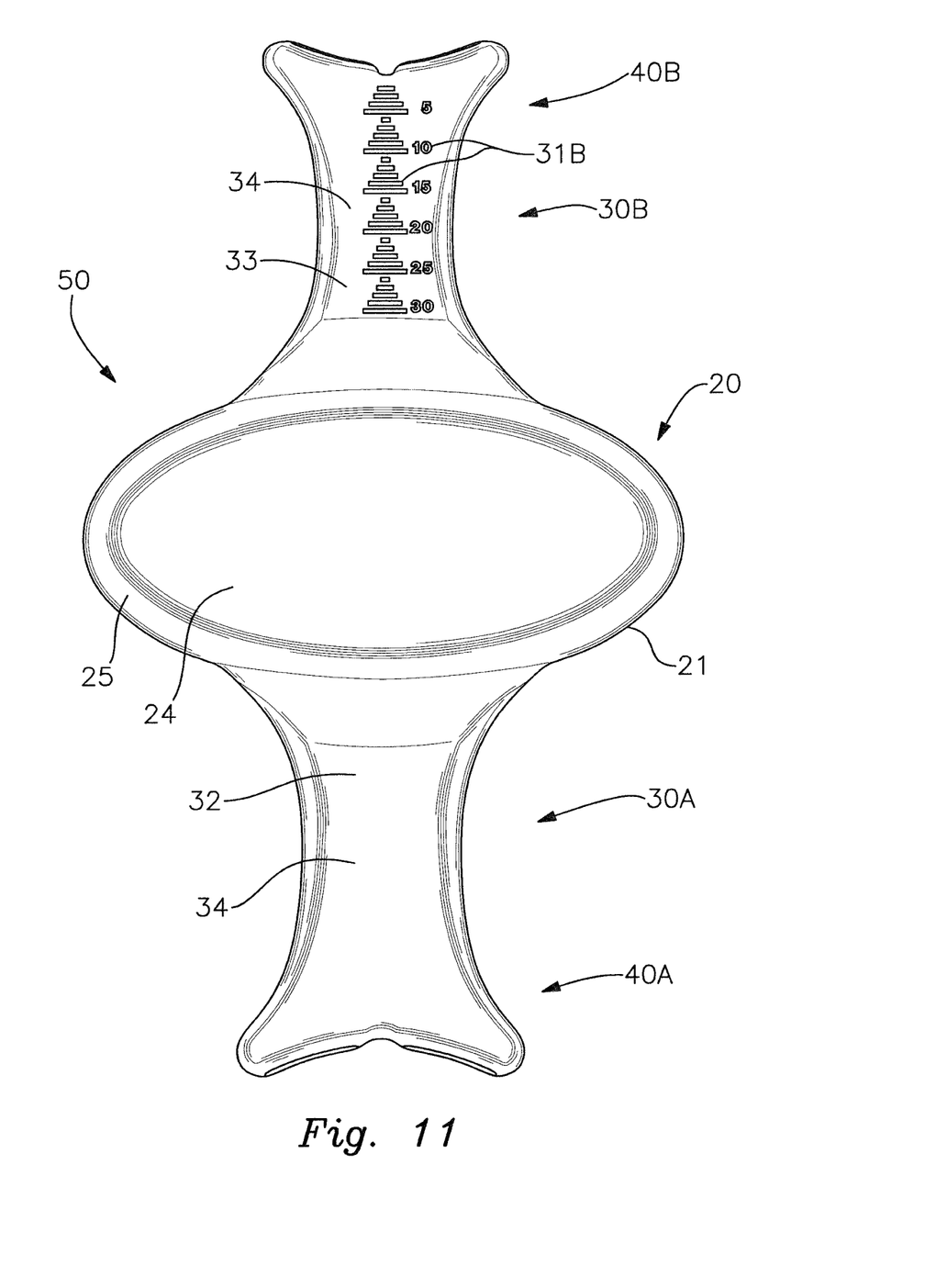
FIG. 11 is a plan view of the embodiment shown in FIG. 10.
Figure 12:
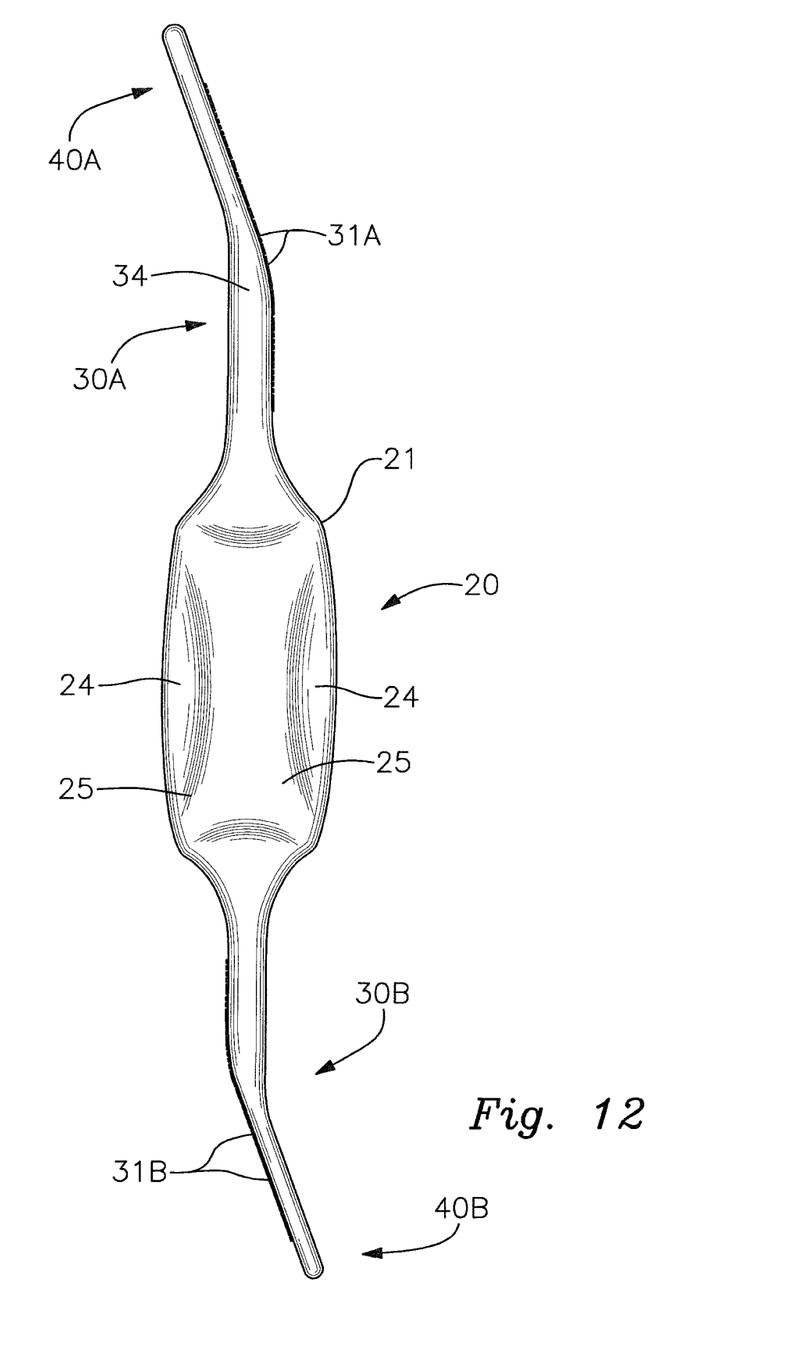
FIG. 12 is a lateral or side view of the embodiment of FIG. 9.

The manipulator end portion 40, in this embodiment being the distal end with the handle portion 20 being the proximal end of the device 10, is connected to the neck portion 30 in a transition zone 34, such that the manipulator end portion 40 is not co-planar with the neck portion 30, the manipulator end portion 40 extending distally and downwardly from the neck portion 30. The transition zone 34 may comprise an angled junction, with an angle of approximately 15-25 degrees having been found as suitable for the transition zone 34, or alternatively the transition zone 34 may comprise a curved junction. A preferred angle for the transition zone is approximately 20 degrees. The manipulator end portion 40 is preferably wider than the neck portion 30, i.e., of greater dimension in the transverse direction, and comprises a concave distal edge 42, a laterally extending manipulator member 43 and a centrally located, longitudinally extending, frenulum recess, groove, notch or slot 41 disposed in the concave distal edge 42. The configuration of the concave edge 42 may have an angular form with linear segments (as shown in FIGS. 1-6) or an arcuate form with curved segments (as shown in FIGS. 7 and 8). The frenulum recess 41 extends longitudinally in the proximal direction from the concave edge 42 and into the manipulator member 43, the shape and size of the frenulum recess 41 chosen so as to be able to receive the frenulum tissue such that the manipulator member 43 is centrally located relative to the tongue. Preferably the frenulum recess 41 is curved rather than angular.

The transition from the neck portion 30 through the transition zone 34 and to the distal end of the manipulator end portion 40 is preferably structured with a gradual increase in the width dimension from proximal to distal, such that the lateral sides of this part of the device present curved edges. In this manner the combination of the elongated neck portion 30 and manipulator end 40 preferably present a "fishtail" configuration.

All corners or edges of the tongue elevator device 10 are beveled, curved or radiused to preclude angular edge or corners. The device 10 is formed of a relative rigid and hard material such that the device 10 does not readily bend when in use, and may be composed of a metal or a plastic that allows for easy cleaning and sterilization.

In an alternative embodiment, as shown in FIGS. 9-12, the tongue elevator device 50 comprises a central handle portion 20 and opposing first and second manipulator end portions 40A/B, each mounted on first and second elongated neck portions 30A/B, the neck portions 30A/B extending from opposite sides of the central handle 20. Each neck portion 30A/B is preferably provided with measuring indicia 31A/B. The main body 21 of the handle portion 20 is preferably formed with a peripheral edge or shoulder 25 bounding a convex or flat interior surface 24. This design provides a single tongue elevator device 10 wherein the size and/or configuration of the manipulator ends 40A/B are of different size or configuration. In the illustrated embodiment, for example, manipulator end portion 40A is wider than manipulator end portion 40B. First manipulating end portion 40A is not co-planar with first neck portion 30A and second manipulating end portion 40B is not co-planar with second neck portion 40A, each of said manipulating end portions 40A/B being joined to said neck portions 30A/B, respectively, through a transition zone 34. Most preferably, the manipulating end portions 40A/B are angled or curved in opposite directions.

To prevent re-connection of the frenulum to the underside of the tongue, the user grasps the handle portion 10 of the tongue elevator device 10 between the thumb and a forefinger or between the thumb and several finger tips. The manipulator end portion 40 is then inserted into the oral cavity under the tongue and pressed against the remaining frenulum tissue, the manipulator end portion 40 being centered such that the frenulum tissue resides in the central frenulum recess 41. The user then exerts sufficient pressure against the frenulum and/or outwardly pulls the tip of the tongue with the user's free hand to elevate and elongate the tongue. The measuring indicia 31 extending along the elongated neck portion 30 provide a visual indication to insure proper elongation of the tongue.

In similar manner, to use the tongue elevator device 50 the user grips the interior surfaces 24 of the handle portion 20 between the thumb and forefinger such that the neck portion 30A or B not being used rests within the user's palm. The remaining neck portion 30A or B is then inserted into the oral cavity beneath the tongue the and elevation/extension procedure is performed as above.

It is understood that equivalents and substitutions for certain elements set forth above may be obvious to those of skill in the art, and therefore the true scope and definition of the invention is to be as set forth in the following claims.

I claim:

1. A tongue elevator device comprising a handle portion, a pair of neck portions and a pair of manipulating end portions, said neck portions connecting said handle portion to said manipulating end portions;
   said handle portion being wider than said neck portions and said manipulating portions; and
   each of said manipulating end portions comprising a distal concave edge and a frenulum recess centrally disposed on said distal concave edge;
   wherein one of said pair of neck portions is a first neck portion and said manipulating end portion is a first manipulating end portion, and wherein the other of said pair of said neck portions is a second neck portion and a second manipulating end portion; and
   wherein said second neck portion is joined to said handle portion opposite from said first neck portion.

2. The device of claim 1, wherein said first neck portion and said first manipulating end portion are not co-planar and said manipulating end portion extends downwardly from said first neck portion.

3. The device of claim 2, wherein
   said second neck portion and said second manipulating end portion are not co-planar and said second manipulating end portion extends from said neck portion in an opposite direction from said first manipulating end portion.

4. The device of claim 1, further comprising measuring indicia located on each of said pair of neck portions.

5. The device of claim 1, wherein said distal concave edge is angular with linear segments.

6. The device of claim 1, wherein said distal concave edge is arcuate with curved segments.

7. The device of claim 1, wherein said first manipulating end portion is joined to said first neck portion at a transition zone.

8. The device of claim 7, wherein said transition zone is angular.

9. The device of claim 8, wherein said transition zone comprises an angle between 15 and 25 degrees.

10. The device of claim 9, wherein said angle is approximately 20 degrees.

11. The device of claim 1, wherein said handle portion is oblong and widest in a transverse direction.

12. The device of claim 1, further comprising measuring indicia located on each of said pair of neck portions and on each of said pair of manipulating end portions.

13. A tongue elevator device comprising a handle portion, a first and second neck portion and a first and second manipulating end portion, said first neck portion connecting said handle portion to said first manipulating end portion and said second neck portion connecting said handle portion to said second manipulating end portion;

said handle portion being wider than said first and second neck portions and said first and second manipulating portions;

each of said manipulating end portions comprising a distal concave edge and a frenulum recess centrally disposed on said distal concave edge;

wherein said first neck portion and said first manipulating end portion are not co-planar and said first manipulating end portion extends downwardly from said first neck portion, and wherein said first manipulating end portion is joined to said first neck portion at a transition zone;

wherein said second neck portion and said second manipulating end portion are not co-planar and said second manipulating end portion extends from said neck portion in an opposite direction from said first manipulating end portion;

wherein said second neck portion is joined to said handle portion opposite from said first neck portion; and     further comprising measuring indicia located on said first and second neck portions and said first and second manipulating end portions.

14. The device of claim 13, wherein said distal concave edge is angular with linear segments.

15. The device of claim 13, wherein said distal concave edge is arcuate with curved segments.

16. The device of claim 13, wherein said transition zone is angular.

* * * * *